United States Patent [19]

Isshiki et al.

[11] Patent Number: 5,395,941
[45] Date of Patent: Mar. 7, 1995

[54] OPTICALLY ACTIVE 1,4-HYDROPYRIDINE COMPOUNDS

[75] Inventors: Kunio Isshiki, Chigasaki; Takashi Nakashima, Yokohama; Hiroshi Tanaka, Chigasaki; Takeo Yoshioka, Ayase, all of Japan

[73] Assignee: Mercian Corporation, Tokyo, Japan

[21] Appl. No.: 216,216

[22] Filed: Mar. 22, 1994

[30] Foreign Application Priority Data

Mar. 26, 1993 [JP] Japan .................................. 5-092265

[51] Int. Cl.$^6$ .......................................... C07D 405/02
[52] U.S. Cl. .................................................... 546/268
[58] Field of Search ................................ 546/268.322

[56] References Cited

FOREIGN PATENT DOCUMENTS 30111 6/1982 Japan .................................. 514/340

OTHER PUBLICATIONS

Chemical Abstracts, vol. 113, No. 17, Abstract 152,264d, Oct. 24, 1990, p. 765, Kim et al.
Charles J. Sih et al., Tetrahedron Letters, 32, 3465 (1991).
Chem. Pharm Bull 39(1) 108–111 (1991).
K. Tamazawa et al. J. Med. Chem. vol. 29, 2504 (1986).
Goldmann et al. Angew Chem. Int. Ed., 30 1559 (1991).
Shibanuma et al., Chem. Pharm. Bull, vol. 28, 2809 (1980).
Achiwa et al., Tetrahedron Letters, 32, 5805 (1991).

*Primary Examiner*—C. Warren Ivy
*Assistant Examiner*—Zinna N. Davis
*Attorney, Agent, or Firm*—Joseph C. Mason, Jr.; Ronald E. Smith

[57] ABSTRACT

Optically active 1,4-dihydropyridine derivatives represented by general formula (I), process for preparing compounds (Ic) (in general formula (I) , $R^1$ is a lower alkyl group), process for preparing compounds represented by general formula (II) by hydrolyzing the compounds (Ic) under acidic conditions, process for preparing compounds represented by general formula (II) by solvolysis, under basic conditions, of compounds represented by general formula (III);

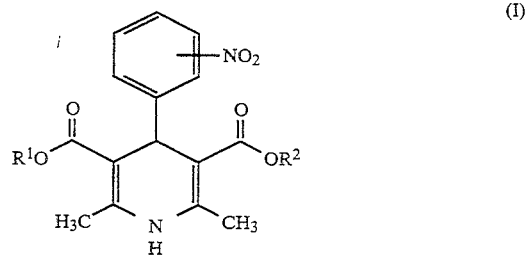

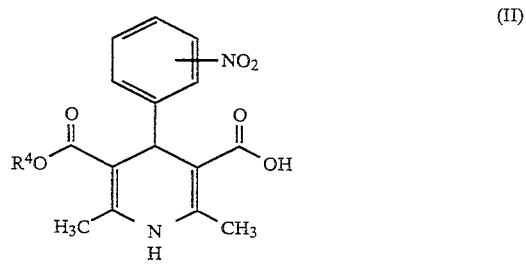

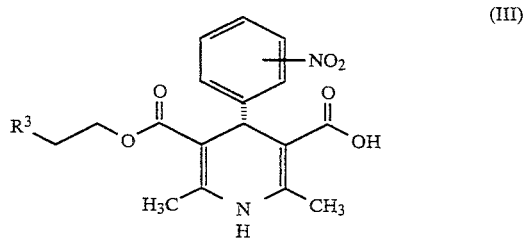

wherein $R^1$ is H, a lower alkyl group, a cyanoethyl group, a lower alkanoylaminoethyl group, or a lower dialkylaminoethyl group; $R^2$ is a 2-tetrahydropyranyl group or a lower alkyloxymethyl group; $R^3$ is a cyano group, a lower dialkylamino group or a lower alkanoylamino group; and $R^4$ is a lower alkyl group. The compounds of general formula (I) and (II) are intermediate compounds for preparing optically active 1,4-dihydropyridine derivatives which are useful as medicines for circulatory organs. The compounds can be produced efficiently by the process of the present invention.

4 Claims, No Drawings

OPTICALLY ACTIVE 1,4-HYDROPYRIDINE COMPOUNDS

TECHNICAL FIELD

The present invention relates to intermediate products for preparing optically active 1,4-dihydropyridine derivatives which are useful as medicines for circulatory organs such as hypotensors and vasodilators.

DESCRIPTION OF THE RELATED ART

Some compounds among optically active 1,4-dihydropyridine derivatives have been known to have a calcium-competing activity, a vasodilating activity and a vasodepressing activity, and such activities are known to be lasting (Arzneim.-Forsch./Drug Res. 38(11), 1666(1988), J. Med. Chem. 29, 2504(1986), Japanese Patent Publication No. 30111/1982), examples of such compounds including (4S)-2,6-dimethyl-4-(3-nitrophenyl)-1,4-dihydropyridine-3,5-dicarboxylic acid. (3S) -3 - (1-benzyl-3-pyrrolidinyl)-ester.methyl ester having the following formula:

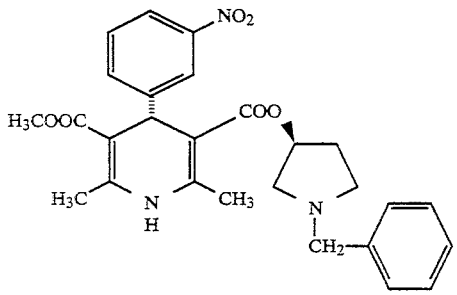

(YM-09730) (J. Med. Chem., 29, 2504(1986)), and (4S)-2,6-dimethyl-4-(3-nitrophenyl)-1,4-dihydropyridine-3,5-dicaraboxylic acid.-3(2-(4-(4-benzhydryl-1-piperazinyl)phenyl)ethyl)ester.5 5-methyl ester having the following formula:

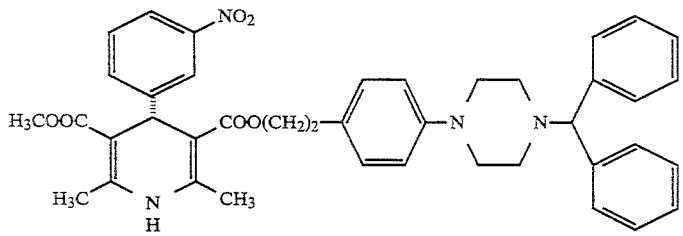

(Chem. Pharm. Bull., 39, 108 (1991)) and their salts.

Reportedly, 1,4-dihydropyridine compounds having different carboxylic acid ester moieties at the 3- and 5-positions of the dihydropyridine ring naturally have asymmetric carbon atoms at the 4-position thereof, and hence there are two kinds of optical isomers which are different in pharmacological activity, in vivo behavior, safety, etc. (K. Tamazawa et al., J. Med. Chem. Vol. 29, 2504 (1986), Angew. Chem. Int. Ed., 30, 1559 (1991)).

From the viewpoint that only one of the isomers that is pharmacologically preferred is to be used as a medicine, investigation has been made to develop a process for preparing optically active 1,4-dihydropyridine compounds. As a general process for preparing the aforementioned optically active 1,4-dihydropyridine compounds which are useful as medicine, there has been known a process in which a preferable ester radical is introduced into a (4R)-1,4-dihydropyridine-3,5-dicarboxylic acid monoester represented by general formula (II)

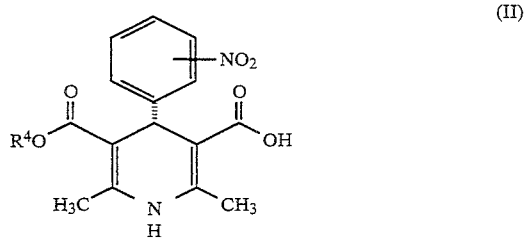

wherein $R^4$ is a lower alkyl group.

As processes for preparing optically active intermediates represented by general formula (II) above, there have been known a chemical method (Shibanuma et al., Chem. Pharm. Bull., Vol. 28, 2809 (1980)), enzymatic processes by Achima et al.(Tetrahedron Letters, 92, 5805 (1991)) and by Charles J. Sih et al. (Tetrahedron Letters, 32, 3465 (1991)).

In the aforementioned chemical process, not only the nitrogen atom on the 1,4-dihydropyridine ring must be protected with a protective group, but also racemic resolution is needed since hydrolysis of ester is not asymmetric hydrolysis. The enzymatic processes required many reaction steps since special compounds such as dipivaloyloxymethyl ester form or diacetoxymethyl ester form are used as substrates.

Under the circumstances, it has been desired to develop a more efficient process for preparing (4R)-1,4-dihydropyridine-3,5-dicarboxylic acid monoesters which are important intermediate compounds for the preparation of optically active 1,4-dihydropyridine derivatives.

With view to solving the above problem, intensive investigation has been made on various enzymes that could asymmetrically hydrolyze symmetric diesters having the following general formula (IV)

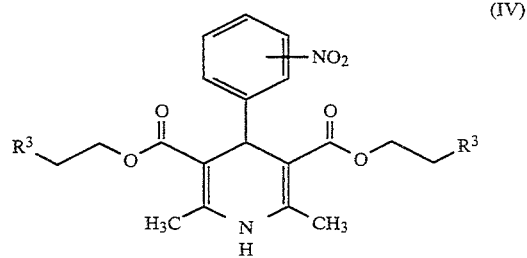

wherein $R^3$ is a cyano group, a lower dialkylamino group, or a lower alkanoylamino group, and as a result it has now been found that certain kinds of microorganism and proteases asymmetrically hydrolyze the aforementioned symmetric diester forms to give rise to optically active 1,4-dihydropyridine-3,5-dicarboxylic acid monoesters represented by general formula (III)

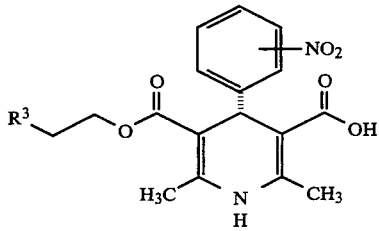
(III)

wherein $R^3$ has the same meaning as defined above).

Further, investigation has been made to find effective protective groups for protecting the carboxyl group of the optically active compounds, with the result that those compounds having carboxyl groups protected as esters with cyclic or straight chain hemiacetal serve as useful intermediate compounds. The present invention has been completed based on this discovery.

SUMMARY OF THE INVENTION

Therefore, the present invention provides optically active 1,4-dihydropyridine derivatives represented by general formula (I)

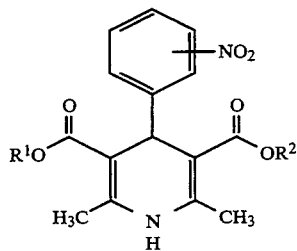
(I)

wherein $R^1$ is a hydrogen atom, a lower alkyl group, a cyanoethyl group, a lower alkanoylaminoethyl group, or a lower dialkylaminoethyl group; and $R^2$ is a 2-tetrahydropyranyl group or a lower alkyloxymethyl group.

Also, the present invention provides a process for preparing the compounds represented by the general formula (I) above, and more particularly a process for preparing optically active 1,4-dihydropyridine derivatives represented by general formula (Ic)

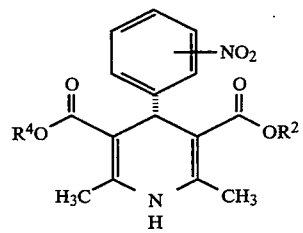
(Ic)

wherein $R^4$ is a lower alkyl group, and $R^2$ has the same meaning as defined above, by solvolysis under basic conditions of optically active 1,4-dihydropyridine derivatives represented by general formula (Ia)

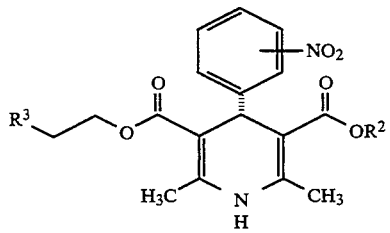
(Ia)

wherein $R^3$ is a cyano group, a lower dialkylamino group or a lower alkanoylamino group; and $R^2$ has the same meaning as defined above.

Further, the present invention provides a process for preparing optically active 1,4-dihydropyridine derivatives represented by general formula (II)

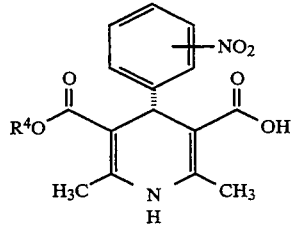
(II)

wherein $R^4$ has the same meaning as defined above, by hydrolyzing under acidic conditions optically active 1,4dihydropyridine derivatives represented by general formula (Ic)

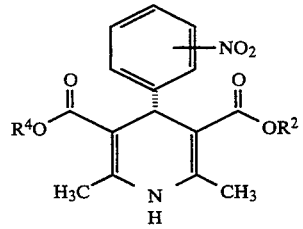
(Ic)

wherein $R^2$ and $R^4$ have the same meanings as defined above, or by solvolysis under basic conditions optically active 1,4-dihydropyridine derivatives represented by general formula (III )

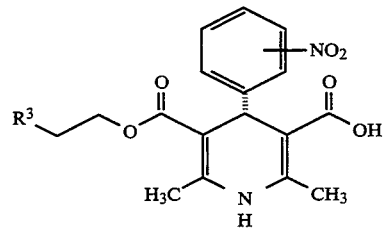
(III)

wherein $R^3$ has the same meaning as defined above.

Hereinafter, the present invention will be described in more detail.

In general formula (I) (general formulas (Ia), (Ib) and (Ic)), $R^1$ is a hydrogen atom, a lower alkyl group, a cyanoethyl group, a lower alkanoylaminoethyl group, or a lower dialkylaminoethyl group.

The lower alkyl group ($R^4$) and the lower alkyl moiety in the lower dialkylaminoethyl group represented by $R^1$ may be straight or branched chain or cyclic and have 1 to 6 carbon atoms, examples of which include a methyl group, an ethyl group, a propyl group, an isopropyl group, a butyl group, a t-butyl group, a cyclohexyl group, etc.

The lower alkanoyl moiety ($R^3$) in the lower alkanoylaminoethyl group represented by $R^1$ may be straight or branched chain and has 1 to 6 carbon atoms, examples of which include a formyl group, an acetyl group, a propionyl group, an isopropionyl group, a butyryl group, an isobutyryl group, a valeryl group, an isovaleryl group, etc.

The lower dialkylamino moiety ($R^3$) in the lower dialkylaminoethyl group represented by $R^1$ includes, for example, a dimethylamino group, a diethylamino group, a dipropylamino group, a diisopropylamino group, a methylethylamino group, a methylpropylamino group, etc.

In general formula I (general formulas (Ia), (Ib) and (Ic)), $R^2$ is a 2-tetrahydropyranyl group or a lower alkyloxymethyl group.

The lower alkyloxymethyl group represented by $R^2$ include a lower alkyl group which may be straight or branched chain and have 1 to 6 carbon atoms, or which may be substituted with an aryl group. Specific examples thereof include a methyloxymethyl group, an ethyloxymethyl group, a propyloxymethyl group, an isopropyloxymethyl group, a benzyloxymethyl group, etc.

The optically active (4R)-1,4-dihydropyridine-3,5-dicarboxylic acid monoesters represented by general formula (III) can be prepared by asymmetrically hydrolyzing the symmetric diester forms represented by general formula (IV) in a phosphate buffer solution containing, for example, a commercially available alkaline protease (produced by Seikagaku Kogyo Co., Ltd., derived from Streptomyces glyceus) and dimethylsulfoxide as a substrate dissolution aid at 27° C.

Of the compounds represented by general formula (I) above, the optically active 1,4-dihydropyridine derivatives represented by general formula (Ia) can be prepared by protecting the respective carboxylic acid moieties of the compounds represented by general formula (III) above obtained by the aforementioned process with a 2-tetrahydropyranyl group or an alkyloxymethyl group. The introduction of protective groups can be performed by a conventional method.

More particularly, the optically active 1,4-dihydropyridine derivatives can be synthesized by reacting the compounds represented by general formula (III) with a) 3,4-dihydro-2H-pyrane in the presence of an inorganic acid, for example, hydrogen chloride, hydrogen bromide, sulfuric acid, etc., or an organic acid, for example, toluenesulfonic acid, methanesulfonic acid, camphorsulfonic acid, trifluoroacetic acid, etc., or b) with a compound represented by general formula (V)

$$X\text{---}CH_2\text{---}OR^5 \qquad (V)$$

wherein $R^5$ is a lower alkyl group, and X is a halogen atom in the presence of an inorganic base, for example, sodium carbonate, potassium carbonate, sodium hydride, etc., or an organic base, for example, triethylamine, pyridine, lutidine, N-methylmorpholine, etc., in an inert solvent, for example, tetrahydrofuran, N,N-dimethylformamide, dioxane, chloroform, toluene, etc., or without solvents.

Here, the lower alkyl group represented by $R^5$ in general formula (V) is a straight or branched chain alkyl group having 1 to 6 carbon. The lower alkyl group may be substituted with an aryl group. Specific examples thereof include a methyl group, an ethyl group, a propyl group, an isopropyl group, a benzyl group, etc. The halogen atom represented by X includes a chlorine atom, a bromine atom, an iodine atom, etc.

Of the compounds of the present invention represented by general formula (I), the dicarboxylic acid diester compounds represented by general formula (Ic) can be prepared by solvolysis of the compounds represented by general formula (Ia) above under basic conditions.

More specifically, the compounds of general formula (Ic) can be prepared by reacting the compounds of general formula (Ia), dissolved in an inert solvent, for example, acetonitrile, tetrahydrofuran, N,N-dimethylformamide, dioxane, etc., or without solvents, in the presence of an inorganic base, for example, sodium hydrogen carbonate, potassium hydrogen carbonate, sodium carbonate, potassium carbonate, etc., and/or an organic base, for example, triethylamine, pyridine, lutidine, N-methylmorpholine, etc., with an alcohol represented by general formula (VI)

$$R^4\text{---}OH \qquad (VI)$$

wherein $R^4$ is a lower alkyl group, at a temperature of 0° to 100° C., preferably 20 to 60° C., or dissolving the compounds of general formula (Ia) in the aforementioned inert solvent or the alcohol of general formula (VI) above, and reacting the solution with an alkoxide represented by general formula (VII)

$$R^4\text{---}OM \qquad (VII)$$

wherein M is an alkali metal, and $R^4$ has the same meaning as defined above, at a temperature of 0° to 100° C., preferably 20° to 60° C.

The dicarboxylic acid diester compounds represented by general formula (Ic) can also be prepared by esterifying the dicarboxylic acid monoester compounds represented by general formula (Ib) under basic conditions.

More specifically, the dicarboxylic acid diester compounds of general formula (Ic) can be prepared by reacting the dicarboxylic acid monoester compounds represented by general formula (Ib) with the alcohol of general formula (VI) above in the presence of a suitable condensing agent; reacting the compounds of general formula (Ib) with a diazo compound such as diazomethane; or reacting acid halide derivatives of the dicarboxylic acid monoester compounds of general formula (Ib) with the alcohol of general formula (VI); or reacting the compound of general formula (Ib) with a desired lower alkyl halide represented by general formula (VIII)

$$R^4\text{---}X \qquad (VIII)$$

wherein $R^4$ and X have the same meanings as defined above, in the presence of an inorganic base, for example, sodium hydrogen carbonate, potassium hydrogen carbonate, sodium carbonate, potassium carbonate, etc., and/or an organic base, for example, triethylamine, pyridine, lutidine, N-methylmorpholine, etc., at a temperature of 0° to 100° C., 5° preferably 20° to 60° C.

The 1,4-dihydropyridine derivatives represented by general formula (II), which are useful as intermediate compounds for preparing medicines, can be prepared according to the process of the present invention, either by hydrolyzing the protective groups of the diester compounds represented by general formula (Ic) under acidic conditions, or by solvolysis of the optically active monoester compounds represented by general formula (III) under basic conditions.

More specifically, the diester compounds represented by general formula (Ic), dissolved in an inert solvent, for example, acetonitrile, tetrahydrofuran, N,N-dimethylformamide, dioxane, etc., or without solvents, can be reacted with water in the presence of an inorganic acid, for example, hydrogen chloride, hydrogen bromide, sulfuric acid, etc., and/or an organic acid, for example, toluenesulfonic acid, methanesulfonic acid, camphorsulfonic acid, trifluoroacetic acid, etc., at a temperature of 0° to 100° C., preferably 20° to 60° C.

The compounds represented by general formula (III), dissolved in an inert solvent, for example, acetonitrile tetrahydrofuran, N,N-dimethylformamide, dioxane, etc., or without solvents, can be reacted with the alcohol represented by general formula (VI) in the presence of an inorganic base, for example, sodium hydrogen carbonate, potassium hydrogen carbonate, sodium carbonate, potassium carbonate, etc., and/or an inorganic base, for example, triethylamine, pyridine, lutidine, N-methyl-morpholine, etc., at a temperature of 0° to 100° C., preferably 20° to 60° C.

Alternatively, the compounds represented by general formula (Ia), dissolved in the aforementioned inert solvent or the alcohol of general formula (VI), can be reacted with the alkoxide of general formula (VII) at a temperature of 0 ° to 100° C., preferably 20° to 60° C.

ADVANTAGES EFFECT OF THE INVENTION

According to the present invention, intermediate compounds for preparing optically active 1,4-dihydropyridine derivatives useful as medicines for circulatory organs such as vasodepressors, vasodilators, etc. can be prepared selectively. That is, the dicarboxylic acid monoesters represented by general formula (II), which are useful intermediate compounds, can be prepared starting from the symmetric diester compounds represented by general formula (IV) via the compounds represented by general formula (I).

Desired diesters which are useful as medicines can be prepared with ease by a known esterification method starting from the optically active 1,4-dihydropyridine derivatives represented by general formula (II) prepared according to the process of the present invention.

EXAMPLES

Hereinafter, the present invention will be described in more detail by examples and reference examples. However, the present invention should not construed as being limited thereto. In the chemical formulae which follow, "THP" is a 2-tetrahydropyranyl group, and "MOM" is a methoxymethyl group.

Reference Example 1

Preparation of (4R)-1,4-dihydro-3-(2-cyanoethyl)oxycarbonyl-2,6-dimethyl-4-(3-nitrophenyl) pyridine-5-carboxylic acid

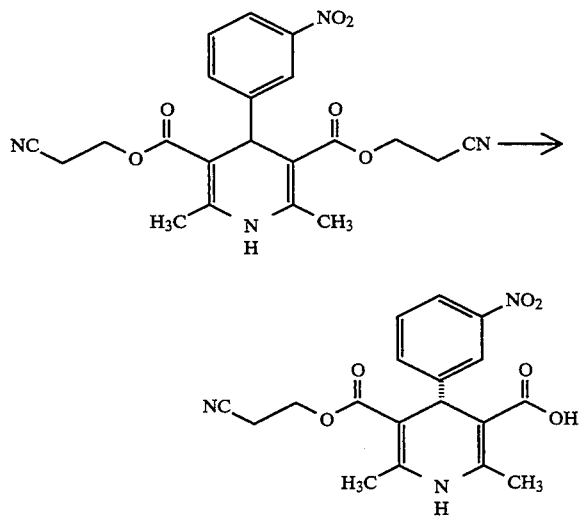

In 20 ml of 0.025M phosphate buffer solution (pH 7.5) having dissolved therein 20 mg of an alkaline protease (EC3.4.2114, prepared by Seikagaku Kogyo Co., Ltd.; derived from Streptomyces griseus) was added 2 ml of a solution of dimethylsulfoxide having dissolved therein 20 mg of bis(2-cyanoethyl) 1,4-dihydro-2,6-dimethyl-4-(3-nitrophenyl)pyridine-3,5-dicarboxylate, and the resulting mixture was stirred at 20° C. for 2 days. The reaction mixture was adjusted to pH 3.0 by addition of 1N hydrochloric acid, followed by addition of 20 ml of ethyl acetate for extraction. The resulting organic layer was washed with saturated saline, and then dried over anhydrous sodium sulfate. After being concentrated under reduced pressure, the concentrate was adsorbed on a preparative TLC (thin layer column chromatography) plate, developed with toluene:acetone (2:1). The fractions showing UV absorption at an Rf value of 0.31 were concentrated to dryness to obtain 5.1 mg of the objective compound.

NMR (Acetone-$d_6$)δ: 2.37(3H,s), 2.40(3H,s) ,2.8–2.9(2H,m), 4.2–4.4(2H,m), 5.18(1H,s),7.51(1H, t,J=8.0 Hz), 7.79(1H,d,J=8.0 Hz), 8.00(1H,d,J=8.0 Hz), 8.17(1H,s), 8.23(1H,br) .

The optical purity of this substance was determined by converting the compound obtained as described above into its methyl ester with diazomethane and comparing the methyl ester with a standard preparation using HPLC [column; chiral AGP, 4×100 mm, mobile phase; 3% isopropanol/0.01M phosphate buffer solution (pH 6.0 ), flow rate; 0.8ml/min.).

The standard preparation was synthesized as follows. That is, 5 mg of (S)-(+)-1,4-dihydro-2,6-dimethyl-5-methoxycarbonyl-4-(3-nitrophenyl)-3-pyridinecarboxylic acid prepared by the method of Shibanuma et al., Chem. Pharm. Bull. 28(9), 2809–2812 (1980) was dissolved in 0.5 ml of tetrahydrofuran, to which was added 6 μl of isobutyl chloroformate. The mixture was stirred for 10 minutes. To the mixture were added 10 μl of ethylene cyanohydrin and 6 μl of triethylamine, and the stirring was continued for additional 2 hours. The reaction mixture was poured in 5 ml of ethyl acetate, and then washed with water. The resulting organic layer was dried over anhydrous sodium sulfate, and concentrated under reduced pressure. The concentrate was adsorbed on a preparative silica gel TLC plate, purified with toluene:acetone (2:1) to synthesize 2-cyanoethyl (R)-1,4-dihydro-2,6-dimethyl-5-methoxycarbonyl-4-(3-nitrophenyl)-3-pyridinecarboxylate. (RS) form was also prepared similarly to the above. Thus, standard preparations were obtained.

Retention time in HPLC was 14.9 minutes for (R) form, and 13.9 minutes for (S) form.

The HPLC analyses indicated that the optical purity of the compound obtained was 100%, stereochemistry of the 4-position was (R). Silica gel TLC of the methyl ester form developed with toluene:acetone (1:1) indicated Rf value of 0.69, and its NMR spectrum was as follows.

$^1$H-NMR (CDCl$_3$) δ:2.38(3H,s), 2.40(3H,s), 2.65(2H,dt,J=2.0 Hz,J=6.0 Hz), 3.65(3H,s), 4.2-4.4(2H,m), 5.10(1H,s), 5.77(1H,br), 7.40(1H, t,J=8.0 Hz), 7.67(1H,td, J=1.0 Hz, J=2.0 Hz, J=8.0 Hz), 8.02(1H,td,J=1.0 Hz,J=2.0 Hz,J=8.0 Hz), 8.10(1H,t,J=2.0 Hz).

Example 1

Preparation of 2-tetrahydropyranyl (4s)-5-(2-cyanoethoxycarbonyl)-1,4-dihydro-2,6-dimethyl-4-(3-nitrophenyl)pyridine-3-carboxylate

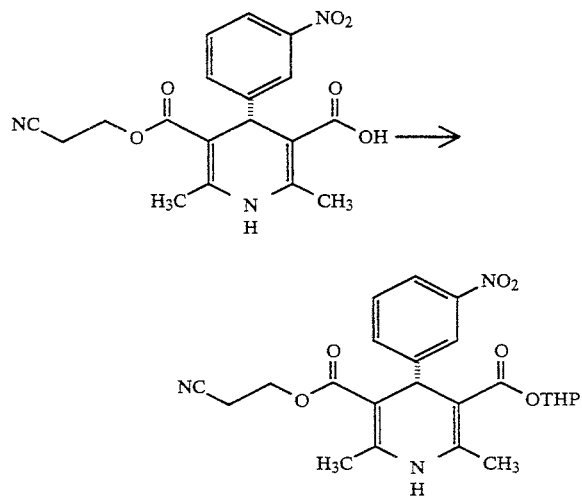

To a solution of 19 mg of (4R)-5-(2-cyanoethoxycarbonyl)-1,4-dihydro-2,6-dimethyl-4 -(3-nitrophenyl )pyridine-3-carboxylic acid in 0.5 ml of tetrahydrofuran were added 5 mg of p-toluenesulfonic acid, and then 0.138 ml of 3,4-dihydro-2H-pyran. The mixture was stirred at room temperature for 5 hours. The reaction mixture was diluted with 5 ml of ethyl acetate, washed with water, and dried over anhydrous Glauber's salt (sodium sulfate), followed by distilling off the solvent under reduced pressure. The residue was purified using preparative TLC to obtain 16.4 mg of the objective compound.

$^1$-NMR (CDCl$_3$)δ: 8.17 & 8.14(1H,t,J=2.2 Hz ), 8.03 & 8.01(1H,dd,J=2.2 Hz,J=1.1 Hz), 7.41 & 7.40(1H, t,J=7.7 Hz), 6.00(1H,brs), 5.92 & 5.91(1H,m), 5.17 & 5.16(1H,s),4.26–4.33(2H,m), 3.89–3.95 & 3.69–3.72(1H,m), 3.46–3.49 & 3.23– 3.29(1H,m), 2.65 & 2.71(2H,m), 2.45 & 2.42(3H,s), 2.39 & 2.37(3H, s), 1.59–1.80(6H,m). [α]$_D$ $^{27}$:+7.93° (c0.82,methanol); MS:FAB (pos.)456(M+1).

Example 2

Preparation of methoxymethyl (4S)-5-(2-cyanoethoxycarbonyl)-1,4-dihydro-2,6-dimethyl -4-(3-nitrophenyl)pyridine-3-carboxylate

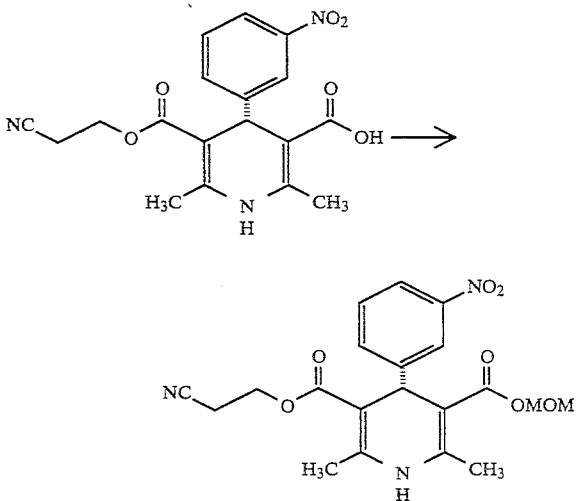

To a solution of 10 mg of (4R)-5-(2-cyanoethoxycarbonyl)-1,4-dihydro-2,6-dimethyl-4-(3-nitrophenyl)pyridine-3-carboxylic acid in 0.5 ml of N,N-dimethylformamide were added 4.3 mg of potassium carbonate, and then 8 μl of chloromethyl methyl ether. The mixture was stirred at room temperature for 5 hours. The reaction mixture was diluted with 5 ml of ethyl acetate, washed with saturated aqueous sodium hydrogen carbonate solution and with water, and dried over anhydrous Glauber's salt (sodium sulfate), followed by distilling off the solvent under reduced pressure the residue was purified using preparative TLC to obtain 3.6 mg of the objective compound.

$^1$H-NMR (CDCl$_3$)δ: 8.13(1H,t,J=7.7 Hz), 8.02(1H,ddd,J=7.7 Hz,J=2.2 Hz,J=1.1 Hz), 7.70(1H,d,J=7.7Hz), 7.41(1H,t,J=7.7 Hz), 5.88(1H,s) , 5.27(1H,d,J=6.2 Hz), 5.17(1H,d,J=6.2 Hz), 5.13(1H,s), 4.28(2H,m) , 3.31(3H,s), 2.67(2H,t,J=5.9 Hz), 2.42(3H,s), 2.40(3H,s)

Example 3

Preparation of (4S)-1,4-dihydro-2,6-dimethyl-5-methoxymethyloxycarbonyl-4-(3-nitrophenyl )pyridine-3-carboxylic acid

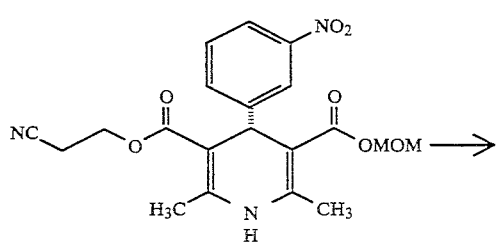

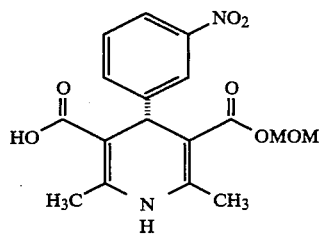

To a solution of 3.6 mg of methoxymethyl (4S)-5-(2-cyanoethoxy-carbonyl)-1,4-dihydro-2,6-dimethyl-4-(3-nitrophenyl)pyridine-3-carboxylate in 0.25 ml of dioxane was added 0.1 ml of 1N aqueous sodium hydroxide solution. The mixture was stirred at room temperature for 1 hour. The reaction mixture was diluted with 5 ml of ethyl acetate, to which were added water and 0.1 ml of 1N aqueous hydrochloric acid. The resulting mixture was dried over anhydrous Glauber's salt (sodium sulfate), followed by distilling off the solvent under reduced pressure to obtain 2.6 mg of the objective compound.

1H-NMR (CD3OD)δ: 8.13(1H,t,J=2.2 Hz), 7.99(1H,ddd,J=7.7 Hz,J=2.2 Hz,J=1.1 Hz), 7.68(1H,d,J=7.7Hz), 7.45(1H, t,J=7.7 Hz), 5.25(1H,d,J=6.2 Hz), 5.13(1H,d,J=6.2 Hz), 5.12(1H,s), 3.26(3H,s), 2.38(3H, s), 2.33(3H,s).

Example 4

Preparation of 2-tetrahydropyranyl (4S)-5-(2-acetamidoethoxycarbonyl)-1,4-dihydro-2,6-dimethyl-4-(3-nitrophenyl)pyridine-3-carboxylate

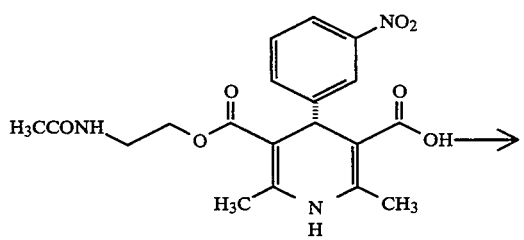

To a solution of 36 mg of (4S)-5-(2-acetamidoethoxycarbonyl)-1,4-dihydro-2,6-dimethyl-4-(3-nitrophenyl)-pyridine-3-carboxylic acid in 0.5 ml of tetrahydrofuran were added 7.7 mg of p-toluenesulfonic acid, and then 0.24 ml of 3,4-dihydro-2-H-pyrane. The mixture was stirred at room temperature for 6 hours. The reaction mixture was diluted with 5 ml of ethyl acetate, washed with saturated aqueous sodium hydrogen carbonate solution and with water, and dried over anhydrous Glauber's salt (sodium sulfate), followed by distilling off the solvent under reduced pressure. The residue was purified using preparative TLC to obtain 18 mg of the objective compound.

1H-NMR (CDCl3OD)δ: 8.17 & 8.14(1H,t,J=2.2 Hz), 8.03 & 8.01(1H,dd,J=2.2 Hz ,J=1.1 Hz), 7.71 & 7.66(1H,dt,J=7.7 Hz, J=1.1 Hz), 6.20(1H,br), 6.00 & 5.90(1H,m), 5.78 & 5.74(1H,br), 4.11–4.23(2H,m), 3.87–3.92 & 3.68–3.77(1H,m), 3.44–3.52(2H,m), 3.44–3.52 & 3.30–3.37(1H,m), 2.43 & 2.42(3H,s), 2.37 & 2.36(3H,s), 1.92 & 90(3H,s), 1.60–1.80(6H,m).

Example 5

Preparation of 2-tetrahydropyranyl (4S)-5-(2-dimethylaminoethoxycarbonyl)-1,4-dihydro-2,6-dimethyl-4 -(3,4-nitrophenyl)pyridine-3-carboxylate

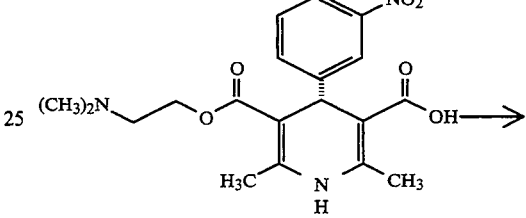

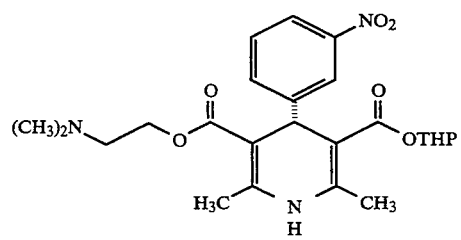

To a solution of 25 mg of (4S)-5-(2-dimethylaminoethoxycarbonyl)-1,4-dihydro-2,6-dimethyl-4-(3-nitrophenyl)pyridine-3-carboxylic acid in 1 ml of tetrahydrofuran were added 5.6 mg of p-toluenesulfonic acid, and then 0.06 ml of 3,4-dihydro-2H-pyrane. The mixture was stirred at room temperature for 6 hours. The reaction mixture was diluted with 5 ml of ethyl acetate, washed with saturated aqueous sodium hydrogen carbonate solution and with water, and dried over anhydrous Glauber's salt (sodium sulfate), followed by distilling off the solvent under reduced pressure. The residue was purified using preparative TLC to obtain 8 mg of the objective compound.

1H-NMR (CDCl3)δ: 8.20 & 8.15(1H,t,J=2.2 Hz), 8.01 & 7.99(1H, dd,J=2.2 Hz ,J=1.1 Hz), 7.75 & 7.69(1H,dt,J=7.7 Hz,J=1.1 Hz), 7.39 & 7.38(1H,t,J=7.7 Hz), 6.00 & 5.91(1H,s), 5.84 & 5.82(1H,s), 4.11–4.19(2H,m), 3.88–3.93 & 3.69–3.74(1H, m), 3.44–3.47 & 3.19–3.26(1H, m), 2.53–2.60(2H,m) 2.44 & 2.42(3H,s), 2.36 & 2.35(3H,s), 2.27(3H,s), 2.25(3H,s), 1.44–1.79(6H,m).

Example 6

Preparation of (4S)-1,4-dihydro-2,6-dimethyl-4-(3-nitrophenyl)-5-(2-tetrahydropyranyloxy)pyridine-3-carboxylic acid

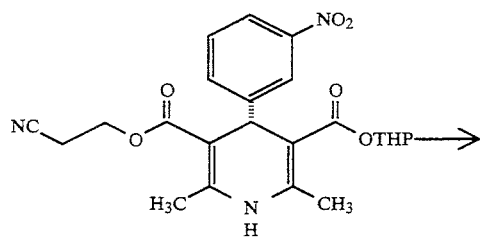

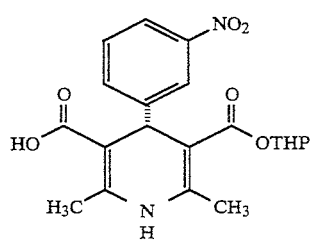

To a solution of 16.4 mg of 2-tetrahydropyranyl (4S)-5-(2-cyanoethoxy-carbonyl)-1,4-dihydro-2,6-dimethyl-4-(3-nitrophenyl)pyridine-3-carboxylate in 1 ml of acetone was added 0.4 ml of 1N aqueous sodium hydroxide solution. The mixture was stirred at room temperature for 1 hour. The reaction mixture was diluted with 5 ml of ethyl acetate, and water was added thereto. The aqueous layer was adjusted to pH 4 with 0.1N hydrochloric acid. After being washed with water, the reaction mixture was dried over anhydrous Glauber's salt (sodium hydroxide), followed by distilling off the solvent under reduced pressure to obtain 14.5 mg of the objective compound.

$^1$H-NMR (CDCl$_3$)δ: 8.17 & 8.13(1H,t,J=2.2Hz), 8.02 & 7.99(1H,dd,J=2.2 Hz,J=1.1 Hz), 7.72 & 7.67(1H,d,J=7.7 Hz), 7.39 & 7.38(1H,t,J=7.7 Hz), 6.00 & 5.90(1H,br), 5.97 & 5.96(1H,br), 5.15 & 5.14(1H,s), 3.88–3.90 & 3.64–3.71(1H,m), 3.43–3.46 & 3.15–3.21(6H,m). 2.38 & 2.37(3H,s), 1.58–1.79(6H,m) . $[\alpha]_D^{27}$ : +54.0° (c0.73, methanol); MS:FAB (neg.)401(M-1) .

Example 7

Preparation of 2-tetrahydropyranyl (4S)-1,4-dihydro-2,6-dimethyl-5-methoxycarbonyl-4-(3-nitrophenyl)pyridine-3-carboxylate (1)

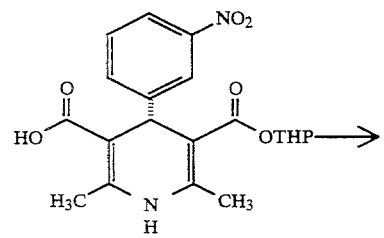

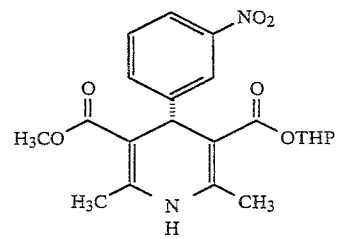

To a solution of 14.5 mg of (4S)-5-(2-tetrahydropyranyloxy)carbonyl-1,4-dimethyl-2,6-dimethyl-4-(3-nitrophenyl)pyridine-3-carboxylic acid in 0.5 ml of methanol was added diazomethane at 0° C., and stirred as it was for 30 minutes. The solvent was distilled off under reduced pressure to obtain 13.8 mg of the objective compound.

$^1$H-NMR (CDCl$_3$)δ: 8.16 & 8.13(1H,t,J=2.2 Hz), 8.02 & 7.99(1H, dd,J=2.2 Hz,J=1.1 Hz), 7.70 & 7.65(1H,d,J=7.7 Hz), 6.00 & 5.89(1H,br), 5.90(1H,br), 5.16 & 5.15(1H,s) , 3.88–3.92 & 3.69–3.75(1H,m), 3.68 & 3.67(3H,s), 3.38–3.52 & 3.18–3.24(1H,s), 2.44 & 2.41(3H,s), 2.36 & 2.34(3H,s) , 1.58–1.80(6H,m); $[\alpha]_D^{27}$: +34.93° (c0.69, methanol); MS:FAB (pos.)417(M+1).

Example 8

Preparation of 2-tetrahydropyranyl (4S)1,4-dihydro-2,6-dimethyl-5-methoxycarbonyl-4-(3-nitrophenyl)pyridine-3-carboxylate (2)

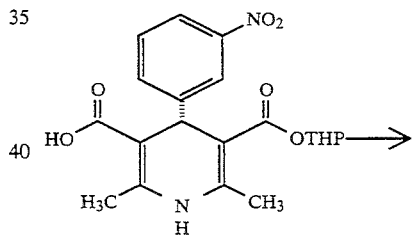

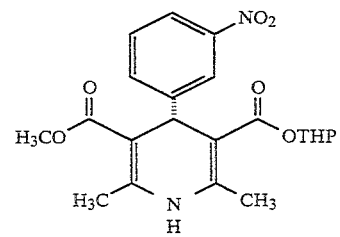

To a solution of 14 mg of (4S)-5-(2-tetrahydropyranyloxy)carbonyl-1,4-dihydro-2,6-dimethyl-4-(3-nitrophenyl)pyridine-3-carboxylic acid in 0.3 ml of N,N-dimethylformamide were added 7.2 mg of potassium carbonate and 0.007 ml of methyl iodide, and the resulting mixture was stirred at room temperature for 1.5 hours. The reaction mixture was diluted with 5 ml of ethyl acetate, washed with water, and dried over anhydrous Glauber's salt (sodium sulfate), followed by distilling off the solvent under reduced pressure to obtain 13.8 mg of the objective compound. This had the same physical and chemical properties as the compound obtained in Example 7.

Example 9

Preparation of 2-tetrahydropyranyl (4S)1,4-dihydro-2,6-dimethyl-5-methoxycarbonyl-4-(3-nitrophenyl)pyridine-3-carboxylate (3)

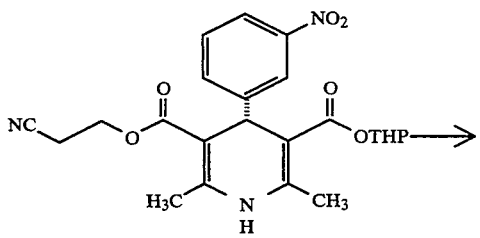

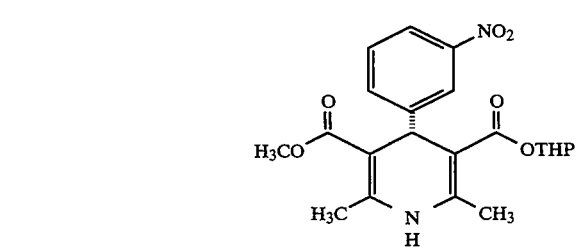

To a solution of 10 mg of 2-tetrahydropyranyl (4S)-5-(2-cyanoethoxycarbonyl)-1,4-dihydro-2,6-dimethyl-4-(3-nitrophenyl)pyridine-3-carboxylate in 0.5 ml of methanol was added 3.5 mg of sodium methoxide. The mixture was stirred at room temperature for 9 hours. The reaction mixture was diluted with 5 ml of ethyl acetate, washed with water, and dried over anhydrous Glauber's salt (sodium sulfate), followed by distilling off the solvent under reduced pressure. The residue was purified by preparative TLC to obtain 2 mg of the objective compound. This had the same physical and chemical properties as the compound obtained in Example 7.

Example 10

Preparation of 2-tetrahydropyranyl (4S)1,4-dihydro-2,6-dimethyl-5-methoxycarbonyl-4-(3-nitrophenyl)pyridine-3-carboxylate (4)

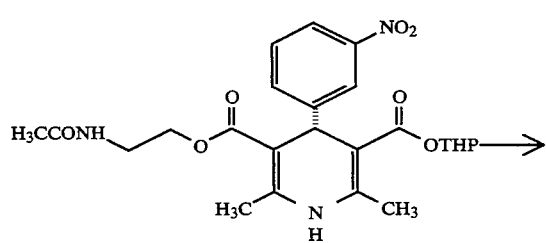

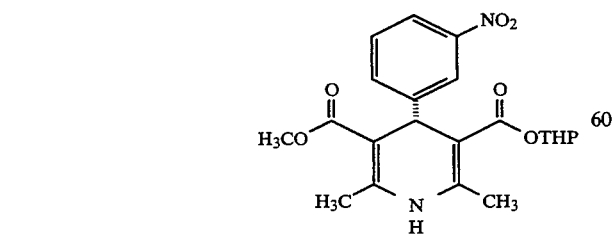

2-Tetrahydropyranyl (4S)-5-(2-acetamidoethoxycarbonyl)carbonyl)-1,4-dihydro-2,6-dimethyl-4-(3-nitrophenyl )pyridine-3-carboxylate (5 mg) was dissolved in 0.2 ml of a methanol solution containing 1M sodium methoxide, and the mixture was stirred for 5 hours on an oil bath at 40° C. The reaction mixture was neutralized with acetic acid, and then concentrated under reduced pressure. The residue thus obtained was purified by preparative TLC to obtain 3.5 mg of the objective compound. This had the same physical and chemical properties as the compound obtained in Example 7.

Example 11

Preparation of 2-tetrahydropyranyl (4S)-1,4-dihydro-2,6-dimethyl-5-methoxycarbonyl-4-(3-nitrophenyl)pyridine-3-carboxylate (5)

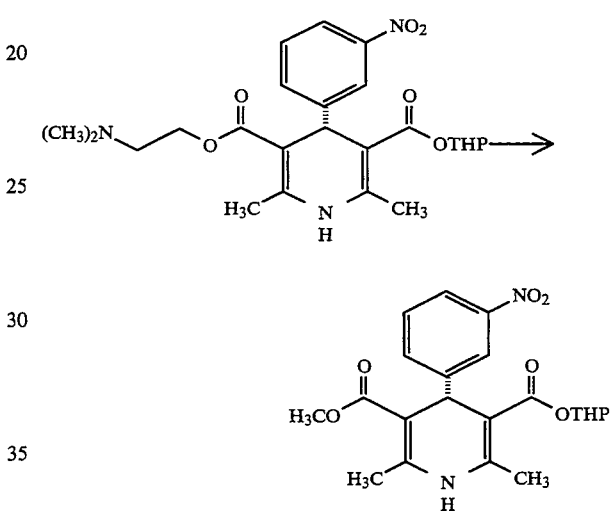

2-Tetrahydropyranyl (4S)-5-(2-dimethylaminoethoxycarbonyl)-1,4-dihydro-2,6-dimethyl-4-(3-nitrophenyl)-pyridine-3-carboxylate (5 mg) was dissolved in 0.2 ml of a methanol solution containing 1M sodium methoxide, and the mixture was stirred for 5 hours on an oil bath at 40° C. The reaction mixture was neutralized with acetic acid, and then concentrated under reduced pressure. The residue thus obtained was purified by preparative TLC to obtain 3.5 mg of the objective compound. This had the same physical and chemical properties as the compound obtained in Example 7.

Example 12

Preparation of (4R)-1,4-dihydro-2,6-dimethyl-5-methoxycarbonyl-4-(3-nitrophenyl)pyridine-3-carboxylic acid (1)

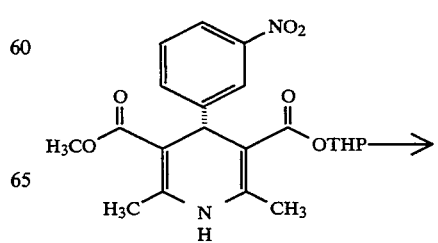

-continued

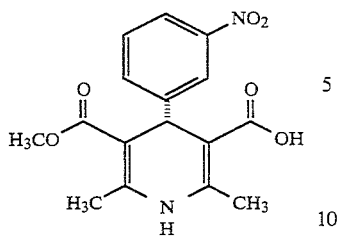

To a solution of 13.8 mg of 2-tetrahydropyranyl (4S)1,4-dihydro-2,6-dimethyl-5-methoxycarbonyl-4-(3-nitrophenyl)pyridine-3-carboxylate in 0.5 ml of ethanol and 0.1 ml of water was added 6 mg of p-toluenesulfonic acid. The mixture was stirred at room temperature for 2 hours. The reaction mixture was diluted with 5 ml of ethyl acetate, washed with water, and dried over anhydrous Glauber's salt (sodium sulfate), followed by distilling off the solvent under reduced pressure. The residue was purified by preparative TLC to obtain 6.0 mg of the objective compound.

$^1$H-NMR (CD$_3$OD)δ: 8.09(1H,t,J=2.2 Hz), 7.99(1H,ddd,J=8.1 Hz, J=2.2 Hz, J=1.1 Hz),7.64(1H,d,J=1.1 Hz), 7.44(1H,t,J=8.1 Hz), 5.09(1H,s), 3.62(3H,s), 2.34(3H,s), 2.33(3H,s); $[\alpha]_D^{27}$: −32.0° (c0.30, methanol); $[\alpha]_D^{27}$: −22.3° (c0.30, acetone); MS:FAB(neg.)331(M−1).

Example 13

Preparation of (4R)-1,4-dihydro-2,6-dimethyl-5-methoxycarbonyl-4-(3-nitrophenyl)pyridine - 3-carboxylic acid (2)

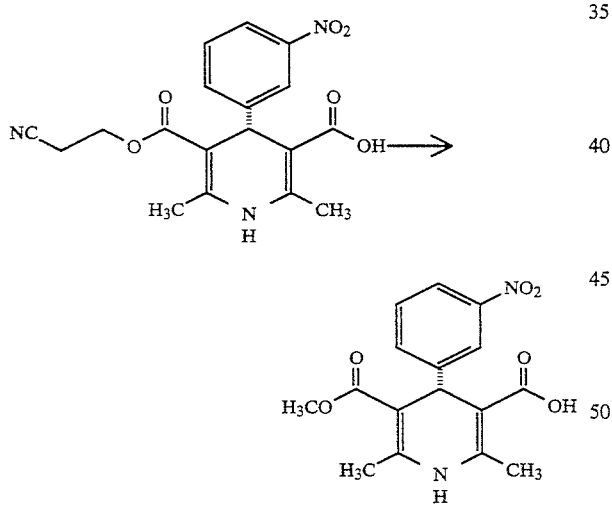

(4R )-1,4-dihydro-3 -(2-cyanoethoxycarbonyl)-2,6-dimethyl-4-(3-nitrophenyl)pyridine-3-carboxylic acid (10.0 mg) was dissolved in 1 ml of a methanol solution containing 1M sodium methoxide, and the mixture was stirred for 4 hours on an oil bath at 50° C. Under cooling the reaction mixture, 1N hydrochloric acid was added thereto to render pH 2, and 5 ml of deionized water and 5 ml of ethyl acetate were added to the mixture, followed by separation. The resulting organic layer was washed with water, and dried over anhydrous Glauber's salt (sodium sulfate), followed by distilling off the solvent under reduced pressure. The residue was thus obtained was purified by preparative TLC to obtain 4.0 mg of the objective compound. This had the same physical and chemical properties as the compound obtained in Example 12.

Example 14

Preparation of (4R)-1,4-dihydro-2,6-dimethyl-5-methoxycarbonyl-4-(3-nitrophenyl)pyridine-3-carboxylic acid (3)

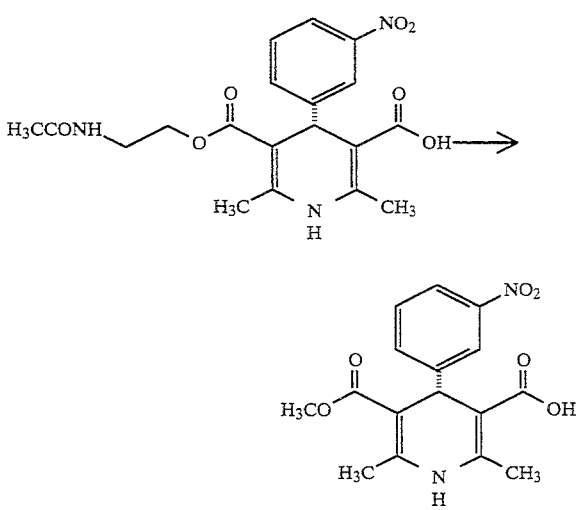

(4R)-5-(2-acetamidoethoxycarbonyl)-1,4-dihydro-2,6-dimethyl-4-nitrophenyl)pyridine-3-carboxylic acid (10.0 mg) was dissolved in 1 ml of a methanol solution containing 1M sodium methoxide, and the mixture was stirred for 5 hours on an oil bath at 40° C. Under cooling the reaction mixture, 1N hydrochloric acid was added thereto to render pH 2, and 5 ml of deionized water and 5 ml of ethyl acetate were added to the mixture, followed by separation. The resulting organic layer was washed with water, and dried over anhydrous Glauber's salt (sodium sulfate), followed by distilling off the solvent under reduced pressure. The residue was thus obtained was purified by preparative TLC to obtain 8.0 mg of the objective compound. This had the same physical and chemical properties as the compound obtained in Example 12.

What is claimed is:

1.) pyridine Optically active 1,4-dihydropyridine compound represented by formula (I)

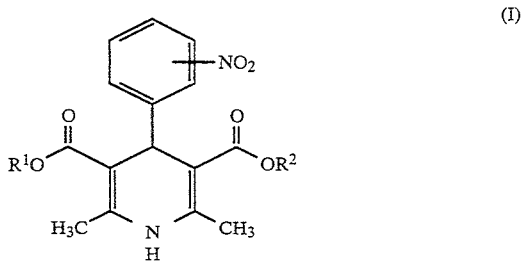

wherein $R^1$ is a hydrogen atom, a lower alkyl group, a cyanoethyl group, a lower alkanoylaminoethyl group, or a lower dialkylaminoethyl group; and $R^2$ is a 2-tetrahydropyranyl group.

2. The optically active 1,4-dihydropyridine compound represented by formula (Ia)

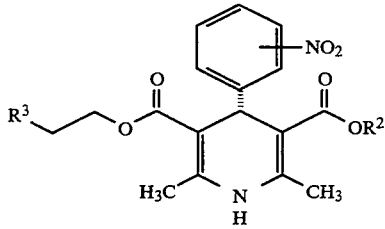

wherein $R^2$ is a 2-tetrahydropyranyl group; and $R^3$ is a cyano group, a lower dialkylamino group, or a lower alkanoylamino group.

3. The optically active 1,4-dihydropyridine compound represented by formula (Ib)

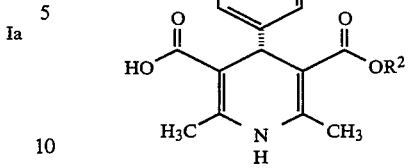

wherein $R^2$ is a 2-tetrahydropyranyl group.

4. The optically active 1,4-dihydropyridine compound represented by formula (Ic)

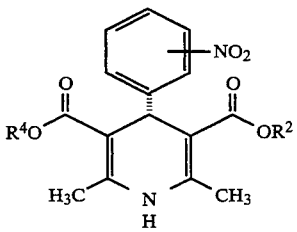

wherein $R^2$ is a 2-tetrahydropyranyl group: and $R^4$ is a lower alkyl group.

* * * * *

UNITED STATES PATENT AND TRADEMARK OFFICE
CERTIFICATE OF CORRECTION

PATENT NO. : 5,395,941

DATED : March 7, 1995

INVENTOR(S) : Kunio Isshiki, Takashi Nakashima, Hiroshi Tanaka, Takeo Yoshioka

It is certified that error appears in the above-indentified patent and that said Letters Patent is hereby corrected as shown below:

On title page, and col. 1,
Title: [54] "OPTICALLY ACTIVE 1,4-HYDROPYRIDINE COMPOUNDS" should read "OPTICALLY ACTIVE 1,4-DIHYDROPYRIDINE COMPOUNDS"

Column 1, line 21, "acid." should read "acid."

Column 1, line 22, "ester." should read "ester."

Column 1, line 39, "acid." should read "acid."

Column 1, line 40, "ester." should read "ester."

Column 2, line 21, "Achima" should read "Achiwa"

Column 2, line 21, "92" should read "32"

Column 4, line 31, "as defined" should read "as $R^4$ defined"

Column 4, line 33, "1,4dihydropyridine" should read "1,4-dihydropyridine"

UNITED STATES PATENT AND TRADEMARK OFFICE
CERTIFICATE OF CORRECTION

PATENT NO. : 5,395,941
DATED : March 7, 1995
INVENTOR(S) : Kunio Isshiki, Takashi Nakashima, Hiroshi Tanaka, Takeo Yoshioka It is certified that error appears in the above-indentified patent and that said Letters Patent is hereby corrected as shown below:

Column 8, line 34, "(3-nitrophenyl)pyridine" should read "(3-nitrophenyl)-pyridine"

Column 8, line 35, "20°" should read "27°"

Column 9, line 27, "(4s)" should read "(4S)"

Column 9, line 63, "1-NMR" should read "$^1$H-NMR"

Column 10, line 32, "(3-nitrophenyl)pyrin-" should read "(3-nitrophenyl)-"

Column 12, line 1, "(CDCl$_3$OD)" should read "(CD$_3$OD)"

Column 12, line 9, "1.92 & 90(3H,s)" should read "1.92 & 1.90(3H,s)"

Column 12, line 16, "(3,4-nitrophenyl)" should read "(3-nitrophenyl)"

Column 13, line 48, "(6H,m)." should read "(1H,m), 2.45 & 2.42 (3H,m),"

UNITED STATES PATENT AND TRADEMARK OFFICE
CERTIFICATE OF CORRECTION

PATENT NO. : 5,395,941
DATED : March 7, 1995
INVENTOR(S) : Kunio Isshiki, Takashi Nakashima, Hiroshi Tanaka, Takeo Yoshioka It is certified that error appears in the above-indentified patent and that said Letters Patent is hereby corrected as shown below:

Column 15, line 66, "2-Tetrahydropyranyl (4S)-5-(2-acetamidoethoxycarbonyl)carbonyl)-1,4-dihydro-2,6-dimethyl-4-(3-nitrophenyl)pyridine-3-carboxylate" should read "2-Tetrahydropyranyl (4S)-5-(2-acetamidoethoxycarbonyl)-1,4-dihydro-2,6-dimethyl-4-(3-nitrophenyl)-pyridine-3-carboxylate"

Column 18, line 31, "2,6-dimethyl-4-nitrophenyl)pyridine-3-carboxylic acid" should read "2,6-dimethyl-4-(3-nitrophenyl)pyridine-3-carboxylic acid"

Column 18, line 48, "1.) pyridine Optically active 1,4-dihydropyridine" should read "1. Optically active 1,4-dihydropyridine"

Signed and Sealed this

Second Day of January, 1996

Attest:

BRUCE LEHMAN

Attesting Officer          Commissioner of Patents and Trademarks